(12) United States Patent
Meinig

(10) Patent No.: US 8,770,208 B2
(45) Date of Patent: Jul. 8, 2014

(54) TREATMENT OF HEAD LICE INFESTATIONS

(76) Inventor: Kelly Meinig, Seattle, WA (US)

( * ) Notice: Subject to any disclaimer, the term of this patent is extended or adjusted under 35 U.S.C. 154(b) by 0 days.

(21) Appl. No.: 13/542,578

(22) Filed: Jul. 5, 2012

(65) Prior Publication Data

US 2013/0012581 A1    Jan. 10, 2013

Related U.S. Application Data

(60) Provisional application No. 61/505,359, filed on Jul. 7, 2011.

(51) Int. Cl.
  *A45D 7/00*  (2006.01)
  *A45D 7/02*  (2006.01)
  *A45D 24/16* (2006.01)

(52) U.S. Cl.
  USPC ............................ 132/212; 132/200; 132/120

(58) Field of Classification Search
  CPC .................. A45D 24/02; A45D 24/30; A45D 2019/0033; A45D 2024/345
  USPC .............. 132/212, 213, 213.1, 214, 219, 125, 132/148, 270; 43/133; 3/212, 213, 213.1, 3/214, 219, 125, 148, 270
  See application file for complete search history.

(56) References Cited

U.S. PATENT DOCUMENTS

| | | | |
|---|---|---|---|
| 3,272,208 A * | 9/1966 | Hasselbusch, Jr. | ........... 132/212 |
| D274,658 S | 7/1984 | Saferstein et al. | |
| D275,804 S | 10/1984 | Saferstein et al. | |
| 4,502,498 A | 3/1985 | Saferstein et al. | |
| 4,540,711 A | 9/1985 | Bettarini et al. | |
| 4,671,303 A | 6/1987 | Saferstein et al. | |
| D336,540 S | 6/1993 | Doran | |
| D353,225 S | 12/1994 | Doran et al. | |
| 5,547,665 A | 8/1996 | Upton | |
| 5,584,309 A | 12/1996 | De Beneditis et al. | |
| D408,240 S | 4/1999 | Garcia | |
| 5,968,507 A | 10/1999 | Upton | |
| 5,972,987 A | 10/1999 | Reid et al. | |
| 6,006,758 A | 12/1999 | Thorne | |

(Continued)

FOREIGN PATENT DOCUMENTS

GB    2140682    * 12/1984

OTHER PUBLICATIONS

Mahreen Ameen et al., Oral Ivermectin for Treatment of Pediculosis Capitis, The Pediatric Infections Disease Journal, vol. 29, No. 11, pp. 991-993, Nov. 2010, 3 pages.

(Continued)

*Primary Examiner* — Rachel Steitz
(74) *Attorney, Agent, or Firm* — Lowe Graham Jones PLLC

(57) ABSTRACT

Techniques and apparatus for treating head lice infestations are described. Some embodiments include a nit (louse egg) detection plate that provides a surface against which irregularities of a hair of a person are more apparent to a viewer than without the detection plate. The detection plate may also include a serrated edge that is operable to separate hairs of the person for viewing over the detection plate. Other embodiments provide a method for using the detection plate to detect and remove nits from hairs of a person. The method may include placing a thin layer of hair of a person over the detection plate, detecting nits by viewing the hairs against a backdrop provided by the detection plate, and removing any detected nits.

19 Claims, 19 Drawing Sheets

(56) References Cited

U.S. PATENT DOCUMENTS

| | | |
|---|---|---|
| 6,086,682 A | 7/2000 | Anderson |
| 6,158,443 A * | 12/2000 | Leman et al. .................. 132/120 |
| 6,626,599 B2 | 9/2003 | De Laforcade |
| D493,571 S | 7/2004 | Jenkins |
| 7,021,317 B1 | 4/2006 | Nathaniel |
| 7,090,833 B2 | 8/2006 | Coleman |
| 7,117,873 B2 | 10/2006 | Bacharach et al. |
| 7,234,472 B2 | 6/2007 | Ramet |
| 7,461,661 B2 | 12/2008 | Chudzik et al. |
| 7,631,648 B2 | 12/2009 | Kirby |
| 7,735,497 B2 | 6/2010 | Kim |
| 2004/0037798 A1 | 2/2004 | Coleman |
| 2004/0118424 A1* | 6/2004 | Russell ........................ 132/208 |
| 2005/0051190 A1 | 3/2005 | Bachrach et al. |
| 2006/0248785 A1 | 11/2006 | Shelton |
| 2007/0295350 A1 | 12/2007 | Shelton |
| 2008/0299064 A1 | 12/2008 | Melfi |
| 2009/0223535 A1 | 9/2009 | Teshigawara |
| 2009/0314305 A1 | 12/2009 | Bachrach et al. |
| 2010/0049286 A1 | 2/2010 | Thorsen |

OTHER PUBLICATIONS

C. Balcioglu et al., Plastic Detection Comb Better than Visual Screening for Diagnosis of Head Louse Infestation, Epidemiol. Infect. (2008), 136, 1425-1431, Cambridge University Press, DOI 10.1017/S0950268807000118, Printed in the United Kingdom, accepted Nov. 14, 2007, first published online Jan. 4, 2008, 7 pages.

Health Enterprises, Medi-Comb Lice Comb, N. Attleboro, MA 02760.

Rick Speare et al., Head Lice are not Found on Floors in Primary School Classrooms, Australian and New Zealand Journal of Public Health, vol. 26, No. 3, pp. 208-211, 2002, 4 pages.

Ronni Wolf et al., Treatment of Scabies and Pediculosis: Facts and Controversies, Clinics in Dermatology, vol. 28, pp. 511-518, 2010, 8 pages.

* cited by examiner

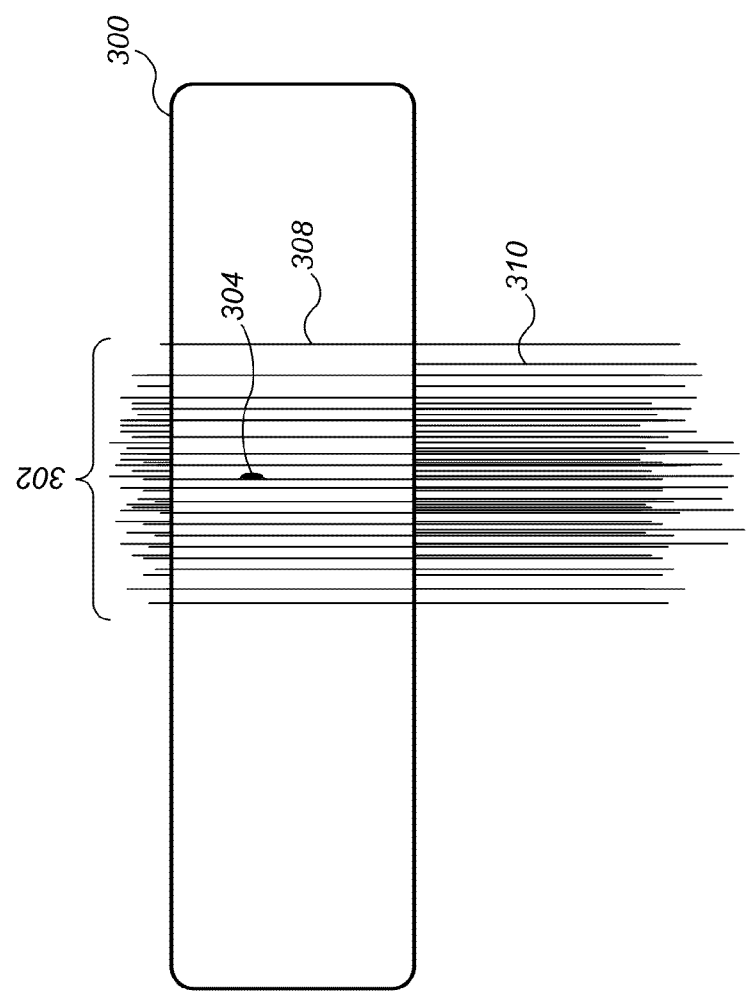

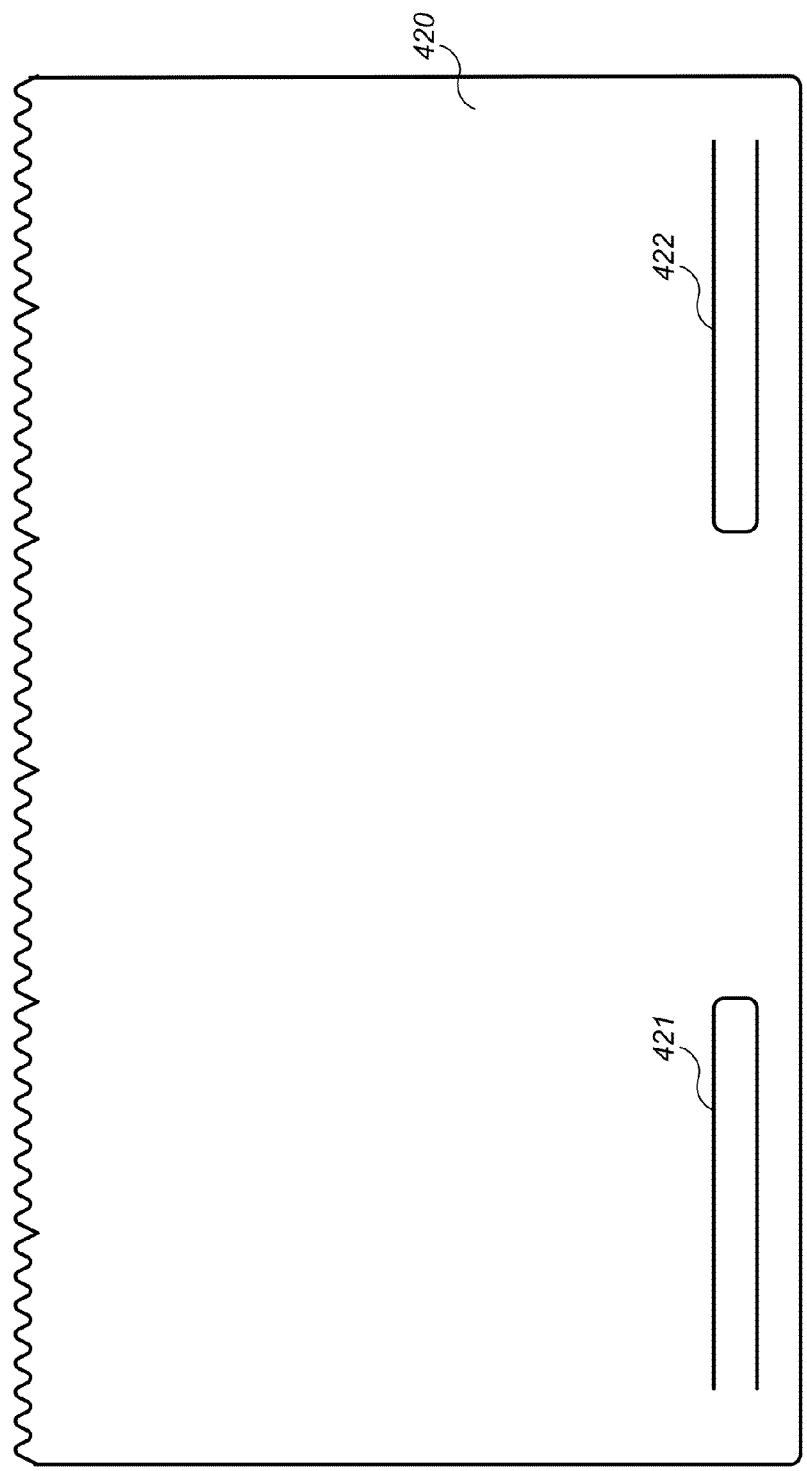

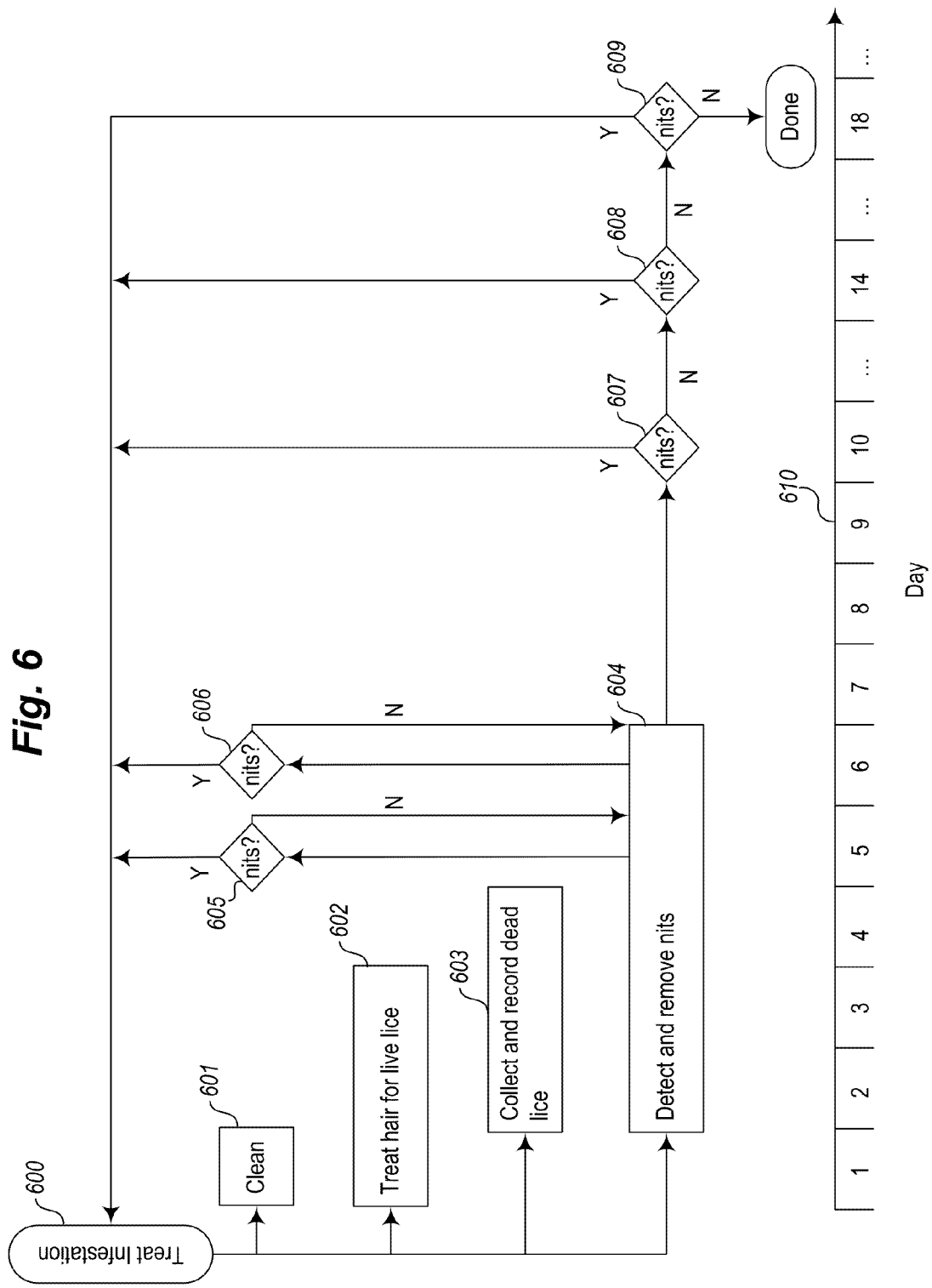

TREATMENT OF HEAD LICE INFESTATIONS

TECHNICAL FIELD

The present disclosure relates to methods, techniques, and apparatus for treating head lice infestations and, more particularly, to methods, techniques, and apparatus for treating head lice infestations using a detection plate to facilitate the detection and/or removal of lice eggs attached to hairs.

BACKGROUND

Head lice infestations ("pediculosis capititis") are a worldwide endemic problem. Although accurate data on the yearly, worldwide number of lice infestations is not available, the U.S. Centers for Disease Control and Prevention estimates that 6 to 12 million infestations occur each year in the United States alone among children 3 to 11 years of age.

FIG. 1A depicts a mature louse. In particular, FIG. 1A is a magnified view of a louse 100. Head lice are tiny, wingless parasitic insects that infest the hair and scalp of humans and can be very difficult to eliminate. They are roughly 2.5-3.5 mm measured along their longest dimension. Lice can be very hard to see, depending on the type of hair they inhabit, and unless there are many of them, due to the speed with which they can travel. It is reported that lice can travel up to 23 cm per minute.

Head lice develop in three stages: nits (lice eggs), nymphs (immature, non-laying adults), and louse (mature, laying adults). Lice eggs are generally reported to take from 7-14 days to hatch into nymphs. Nymphs mature into laying adults about 7-14 days after hatching. Adult lice begin laying eggs 0-2 days thereafter, and live approximately 4-5 weeks total. The louse life cycle appears to vary based on temperature, humidity, food supply, and other factors. Lice obtain nourishment by sucking blood from the scalp. Without access to blood, lice typically survive for 1-2 days, but under favorable conditions, can live up to 4 days.

FIG. 1B depicts a lice infestation in blond hair. More particularly, a number of nits are circled and indicated as 110a-110c. Nits 110a-110c appear to be relatively immature, based on their dark color, which changes from dark brown when they are laid, to light brown or tan as they near hatching, to white or translucent, once the egg sac is empty.

FIGS. 1C and 1D depict nits. Nits are eggs laid by an adult louse in an associated sac that is attached to a human hair. Nits are white when they are first laid, turn brown before they hatch, and are again yellowish-white once they are empty. FIG. 1C shows an egg sac with egg 120 and an empty egg sac 121. The egg sacs are glued firmly onto individual hairs, generally near the scalp, but can also be found 5 or more inches down an individual hair. Nits can survive for up to 10 days away from the scalp. Nits are approximately 0.5-1 mm in length (along the longest dimension) and oval in shape. FIG. 1D shows a nit 130 (circled for presentation) attached to a hair 132 and displayed with respect to a penny coin 131 to illustrate the small size of the nit 130.

Head lice are not, in and of themselves, dangerous, but they do create an intense nuisance and drain on parents', schools', and other's time, energy, finances, and patience, not to mention the discomfort and potential embarrassment experienced by the affected person. Approximately 60% of schools and childcare centers in the U.S. have adopted a "no nit" policy such as one recommended by the National Pediculosis Association (http://www.headlice.org/downloads/nonitpolicy.htm). Adoption of this policy means children cannot attend school if nits (lice eggs or egg sacs) are found in their hair.

No-nit policies are a controversial subject. The American Academy of Pediatrics, for example, has issued a position statement discouraging no-nit policies in schools (http://aappolicy.aappublications.org/cgi/content/full/pediatrics;126/2/392.) Excluding the time and attention given to lice infestations by school teachers and administrators, lice infestations are estimated to result in 12-24 million US dollars lost school days per year for the children along with 4-8 billion US dollars lost per year for missed workdays by parents who have to stay home with them.

It is not known how, exactly, lice are transmitted from one person to another. It is assumed that lice travel (e.g., walk, crawl) from one person to the next and that that this is the most common means of transmission. This does not appear to have been scientifically confirmed, however. Lice do not jump or fly. There appears to be general agreement that infestations are spread from person to person when a person having a lice infestation comes into close contact with someone without lice. Various modes of transmission have been proposed, but none appear to have been definitively confirmed. Transmission may occur, for example, when children play in close proximity of one another during classroom activities (e.g., at play, during group reading time); by sharing infested clothing (e.g., hats, scarves, coats or hair ties); by sharing an infested brush, comb or towel; by sharing a stuffed animal that has been contaminated (i.e., fomite transmission); or by laying their head down against an infested surface (e.g., a pillow or blanket).

Several epidemiological studies have shown no association between head lice and the sharing of combs, brushes, towels, scarves, hats, and/or clothes. The authors of another study concluded that classroom floors are also not instrumental in the transmission of head lice. The research does appear to show that lice, when they feel threatened, will move to the periphery of a hair, ready to drop off if the perceived danger warrants evacuation. This "flea response" appears to be a viable mode of transmission.

Lice can also survive submersion in water, such as in a swimming pool, bath or shower. However, when lice become immersed, they appear to go into statis and clasp firmly to the hair to which they were attached at the time of the immersion, refusing to leave their host. It has been shown that head lice can live up to 19 hours after being immersed in water.

Regardless of how a person acquires lice, getting rid of them is challenging. Some families experience ongoing infestations that last many months or even years. There are three general approaches taken to treat infestations, generally used in combination with one another: chemical treatment, non-toxic suffocation, and manual removal.

Numerous chemical formulations have been developed over the years to get rid of live lice using active ingredients such as: malathion (brand name: Ovide®), permethrin (brand names: NIX®, RID®, A-200®, Clear®), dimethicone (brand name: LiceMD), pyrethrum (brand names: RID, A-200, Clear, Pronto, R & C), phenothrin, lindane (brand name: Kwell®), oral trimethoprim-sulfamethoxazole, phenothrin, piperonyl butoxide, and various combinations thereof. These chemicals are generally intended to act on the central nervous system of lice but are inherently toxic to humans as well, which makes using them undesirable for many. The use of lindane, for example, is highly controversial. It is an organochloride with similar properties as DDT, and is known to cause neurotoxicity and anemia.

The toxicity of these formulations aside, these products may suffer from other problems as well. There have been numerous reports that lice are adapting to the chemicals and developing resistance, much like bacterial resistance to antibiotic use. In addition, the effectiveness of at least some of these products is in doubt. One percent lindane, for example, was shown to have killed only 17% of lice using the recommended application time. Moreover, most of these products only kill live lice—they do not kill live eggs, which will subsequently hatch and require additional treatment. Furthermore, as the chemical treatments continue to be used, resistance is expected to increase.

Alternatively, many people are interested in non-toxic and/or "traditional" methods used to kill lice by suffocating them, including approaches such as: coating hair in olive oil, petroleum jelly (e.g., Vaseline), coconut oil, castor oil, vegetable shortening (e.g., Crisco), and other oils with or without adding benzyl alcohol, herbal oils, essential oils (e.g., lavender, anise, tea tree oil). Commercially available suffocation products include products and compounds such as: Hair-Clean-1-2-3® (a combination of anise, coconut and ylang ylang oils in an alcohol base) and LiceRX (a combination of various oils, lavender, patchouli, camphor, geranium and others). It is thought that the essential oils and alcohol act by "shocking" the openings on the sides of lice that are used for breathing (spiracles), and keeping them open long enough to allow the oil to clog them, thus blocking the opening and leading to suffocation.

Regardless of the treatment used, "nit-picking"—manually finding and removing nits—is always necessary. Each egg sac is affixed to a hair with a glycoprotein glue that acts as an extremely strong cement that is highly resistant to removal. A thorough nit-picking of a head of medium-length hair usually takes from one to two hours to complete. It is generally recommended that nit-picking be performed in direct lighting, posing an added challenge in winter months before and after school hours when lighting is generally not very good. Seeing each and every nit can be virtually impossible in any lighting condition and many, if not most, nits are simply missed. Unfortunately, missing even one viable nit can result in a new round of infestation.

Typically, fine-toothed combs are used to remove nits from a patient's hair. However, such combs often fail to remove all or even a substantial percentage of nits. Moreover, such combs and other devices/systems for lice and nit removal do not help the caretaker effectively find nits in order to visually confirm an infestation diagnosis or assist in manually removing the nits. In one approach, a comb is used in conjunction with a magnifying glass. However, a magnifying glass may cause eye strain and in any event does not support efficient inspection of a large number of hairs. In another approach, product dyeing compound is used to dye nits a fluorescent color, thereby making them easier to see for subsequent removal. However, this technique may have drawbacks including stains, limited applicability to darker colored hair, and the like.

BRIEF DESCRIPTION OF THE DRAWINGS

FIGS. 3A-3B illustrate use of a nit detection plate to facilitate nit detection according to an example embodiment.

FIGS. 4A-4G illustrate nit detection plates according to multiple example embodiments.

FIG. 6 illustrates a lice infestation treatment process according to an example embodiment.

DETAILED DESCRIPTION

Embodiments described herein provide an apparatus and related techniques for using the apparatus to treat head lice infestations. Example embodiments provide a nit detection plate (sometimes referred to as a "detection plate" or "contrast plate") having a surface that provides a background against which an irregularity on a hair of a patient (e.g., person, mammal, subject, or any entity suffering from a lice infestation) is readily detectable. As discussed, existing approaches focus primarily on killing and/or otherwise removing lice from the hair of the patient. Unfortunately, even when all living lice have been removed from the hair of a patient, there may still remain viable eggs that will hatch into a new generation of lice, thereby perpetuating the infestation. Effective and efficient treatment thus benefits from the detection and removal of nits. Unfortunately, owing to their very small size, nits can be very difficult for a caregiver to detect and/or remove.

The detection plate includes a surface that provides contrast against which nits are more readily detectable. By examining patient hairs located, situated, or disposed upon or over the detection plate, the caregiver can efficiently detect and remove nits from the hair of the patient. The detection plate thus advantageously allows a caregiver to treat a lice infestation by eliminating a potential generation of new lice prior to their emergence as nymphs from their eggs. Embodiments of the detection plate may include additional or alternative features that may further facilitate detection and removal of nits. For example, a detection plate may include serrations or "spreaders" configured to facilitate the manipulation and inspection of a layer of hair for nits. As another example, a detection plate may include clips or other fasteners to attach the plate to the patient, the caregiver, or some other surface or location, so that the detection plate may be operated in a "hands free" manner, such as while a detected nit is being removed from a hair. These and other features, alone or in combination, provide distinct advantages over the traditional method of using a fine-toothed comb, including a greater number or percentage of nits removed in each treatment cycle, less time spent on each treatment cycle, and the like.

Figure 1A:
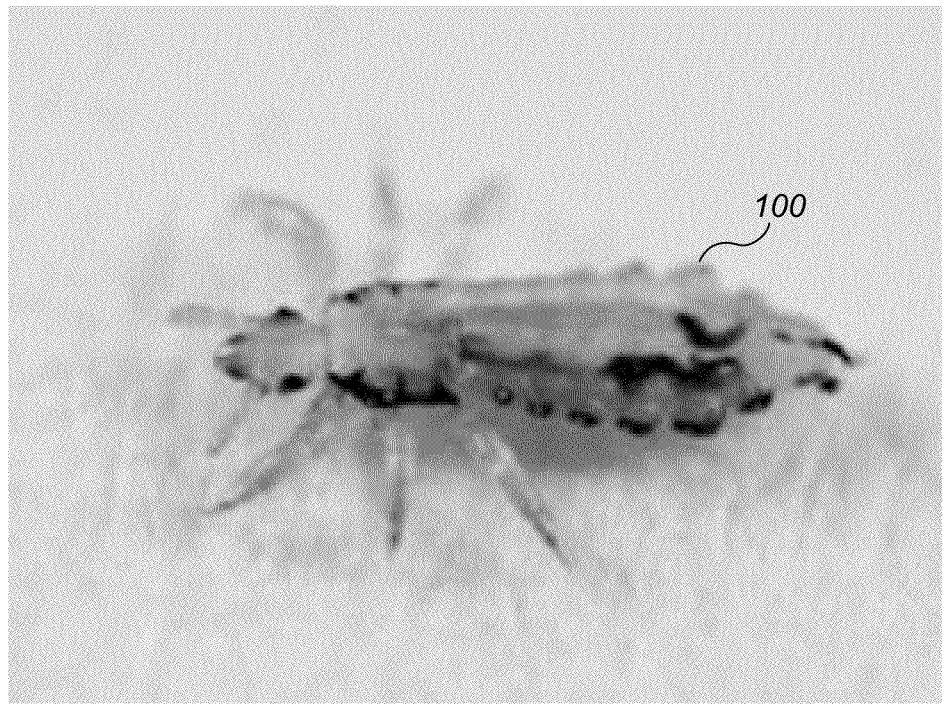
FIGS. 1A-1D show views of head lice and nits.
Figure 1B:
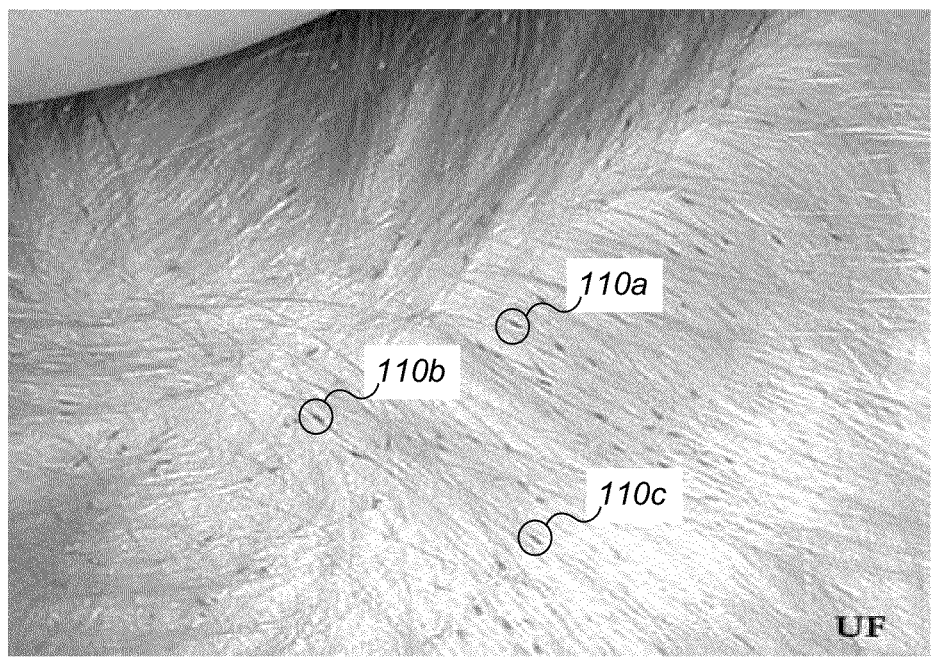
Figure 1C:
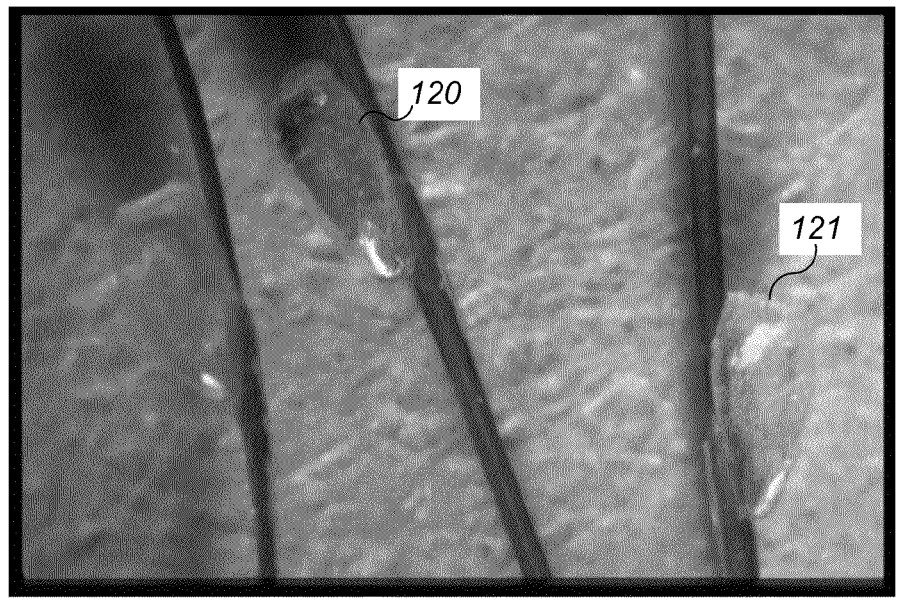
Figure 1D:
Figure 2:
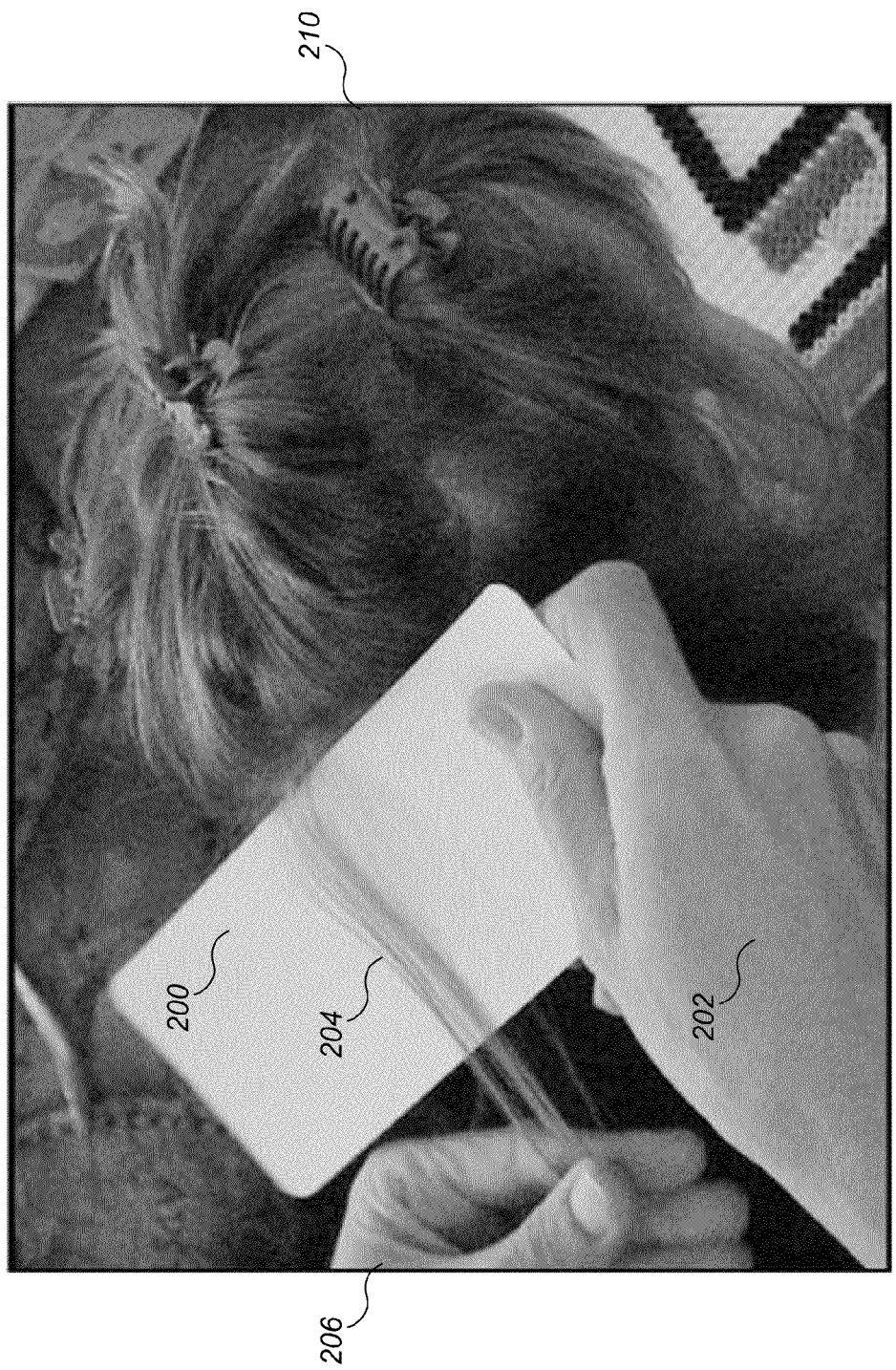
FIG. 2 illustrates use of a nit detection plate according an example embodiment.

FIG. 2 illustrates use of a nit detection plate according an example embodiment. More specifically, FIG. 2 illustrates a detection plate being used to detect nits in the hair of a patient. In particular, FIG. 2 shows a detection plate 200 placed adjacent to a head 210. A caregiver holds the detection plate 200 in her right hand 202 while holding a group of hairs 204 in her left hand 206. The group of hairs 204 is selected as a thin layer and laid over the detection plate 200. The caregiver views the hairs 204 against a contrasting backdrop provided by the detection plate 200. When viewed against the detection plate 200, irregularities in the hairs 204 are more readily visible than when the hairs 204 are not viewed against the detection plate, such as when the hairs 204 are viewed against the scalp or other hairs of the patient. The detection plate 200 is typically made from a material that is at least somewhat flexible yet consistently returns to an original (e.g., flat or slightly curved) shape, such as stiff paper, cardboard, plastic, or the like.

Figure 3B:
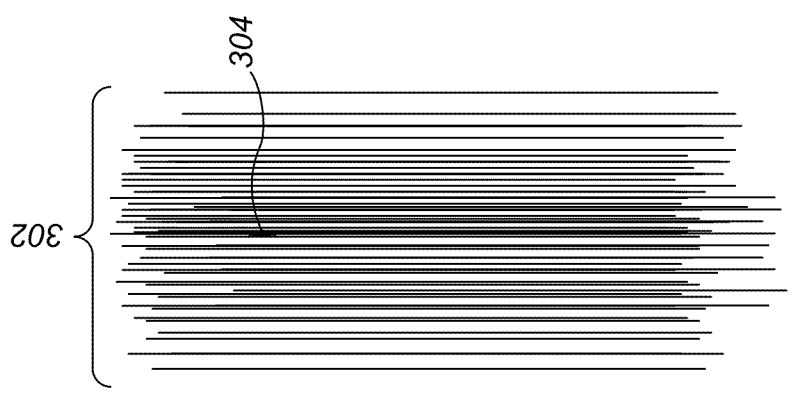

FIGS. 3A-3B illustrate use of a nit detection plate to facilitate nit detection according to an example embodiment. More particularly, FIGS. 3A and 3B illustrate nit detection with and without use of a detection plate. FIG. 3A shows a detection plate 300 located within a group of hairs 302. Note that some of the hairs 302, such as hair 308, are arranged over the detection plate 300, while other of the hairs 302, such as hair 310, are located under the detection plate 300. FIG. 3A further illustrates a nit 304 attached to one of the hairs 302. Typically, the caregiver arranges a layer of hair over the detection plate, in order to confirm the presence or absence of nits in the layer of hair. The thicker the layer of hair, the more difficult it may become to identify a nit, because some hairs of the layer may obscure the view of nits attached to other hairs of the layer. Thus, a thin (e.g., no more than 3 mm, no more than 6 mm, no more than 10 mm) layer of hair is typically utilized. The particular thickness of the layer may depend on various factors, including light conditions, hair color, thickness, fineness, oiliness, or the like.

FIG. 3B shows the group of hairs 302 without the nit detection plate 300. The nit 304 is barely visible amongst the hairs 302, as compared to the view in FIG. 3A where the detection plate 300 is in place. Without the detection plate 300, the nit 304 is obscured by, or difficult to see in the presence of, other of the hairs 302 that were not in view when the hairs 302 were separated into two groups positioned respectively above and below the plate 300. In particular, the hairs that were located below the detection plate 300, as shown in FIG. 3A, here provide a backdrop against which the nit 304 is more difficult to detect. The detection plate 300 thus not only provides a high contrast surface against which the nit or other irregularity (e.g., louse, nymph; empty egg sac; particle, broken, bent, or discolored hair) of the patient's hair will stand out, but also a mechanism for isolating a thin layer of hair, thereby lessening the chance that the nit 304 will be obscured by other hairs.

Figure 4A:
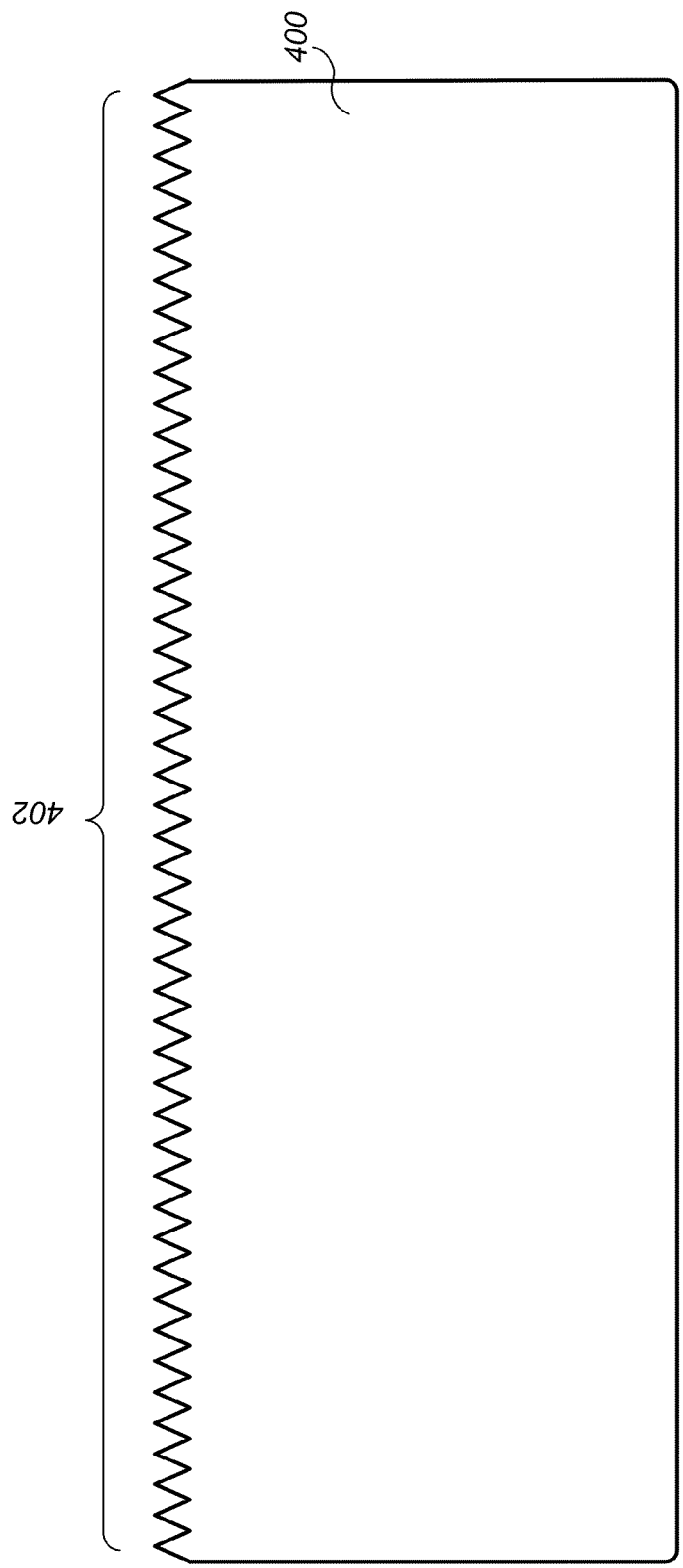

FIGS. 4A-4G illustrate nit detection plates according to multiple example embodiments. FIG. 4A illustrates a nit detection plate 400 according to a first embodiment. The illustrated nit detection plate 400 is substantially flat or planar. In other embodiments, the nit detection plate 400 may be curved so that it conforms to the shape of the patient's head. The nit detection plate 400 includes a serrated (e.g., toothed, jagged, bumpy) edge 402. The serrated edge 402 includes multiple serrations, teeth, points, or bumps that are adapted to separate the hairs of a patient. In one embodiment, each serration is 1-2 mm in length, and separated from adjacent serrations by 1-2 mm, measured from the tip (or peak) of one serration to the tip of an adjacent serration. In another embodiment, each serration is 2-4 mm in length, and separated from adjacent serrations by 2-4 mm. In another embodiment, each serration is 4-7 mm in length, and separated from adjacent serrations by between 1-5 mm. Other ranges or dimensions are contemplated, including serrations having a length under 1 mm and/or separated by less than 1 mm; a length under 4 mm and/or separated by 3-6 mm; having a length and/or separation of no more than 3 mm; having a length and/or separation of more than 3 mm; having a length and/or separation of more than 6 mm; and the like. The serrations of the edge 402 also function to hold hairs in place against one edge (e.g., the head-facing edge) of the detection plate 400, so that when the caregiver manipulates the hairs, such as by moving them from left to right, they do not stay together in a clump or group but rather separate over the detection plate 400, so that the caregiver can better detect nits.

Figure 4B:
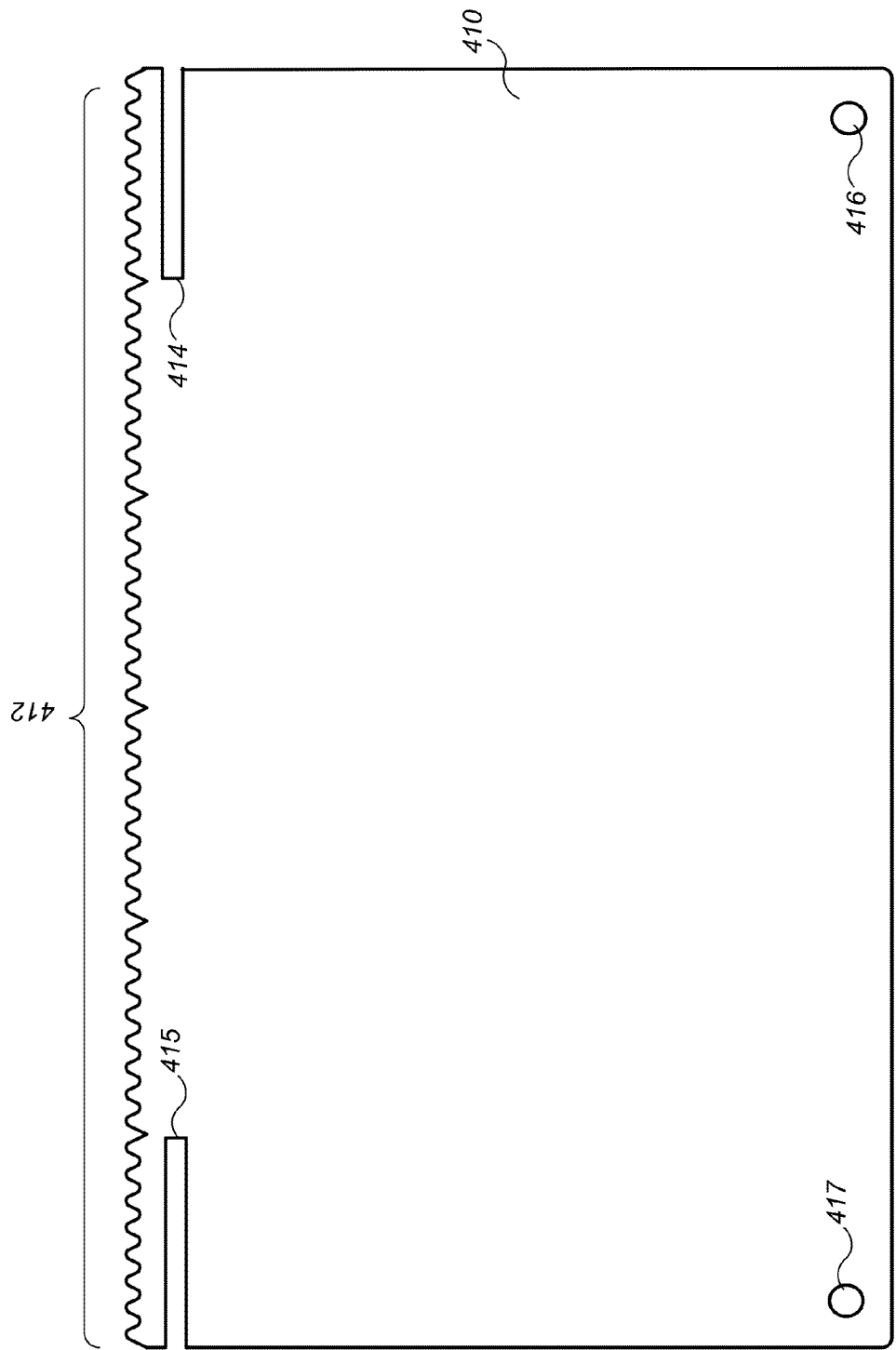

FIG. 4B illustrates a nit detection plate 410 according to a second example embodiment. The nit detection plate 410 also includes a serrated edge 412 having serrations dimensioned similarly to those of serrated edge 402 (FIG. 4A). The serrated edge 412 differs from serrated edge 402 in that the serrations of edge 412 are rounded at their tips. The nit detection plate 410 also includes cutouts 414 and 415. The cutouts can be used by the caregiver to removably attach a clip to the detection plate 410 and to the patient's hair, so that the detection plate 410 can be fixed in place on the patient's head while the caregiver uses her hands to perform some other function.

The nit detection plate 410 further includes holes 416 and 417. The holes 416 and 417 can be used as attachment points for a string, strap, or other holder with which the nit detection plate 410 can be attached to the caregiver. For example, a string attached to holes 416 and 417 can be looped over the head and neck of the caregiver (or clipped to clothing of the caregiver) so that the caregiver need not place the detection plate 410 down on a table or other surface when he is using his hands to perform other functions, such as removing a nit from the hair of the patient.

FIG. 4C illustrates a nit detection 420 plate according to a third example embodiment. The nit detection plate 420 includes clips 421 and 422. The clips 421 and 422 are spring clips affixed to, and situated on one side (here, the facing side) of, the detection plate 420. The caregiver can slide a group of hair between the detection plate 420 and one of the clips 421 or 422. Once the group of hairs has been so placed, the detection plate 420 will tend to remain in place even when the caregiver ungrasps the detection plate in order to perform some other function, such as removing a nit from the hair the patient.

Figure 4D:
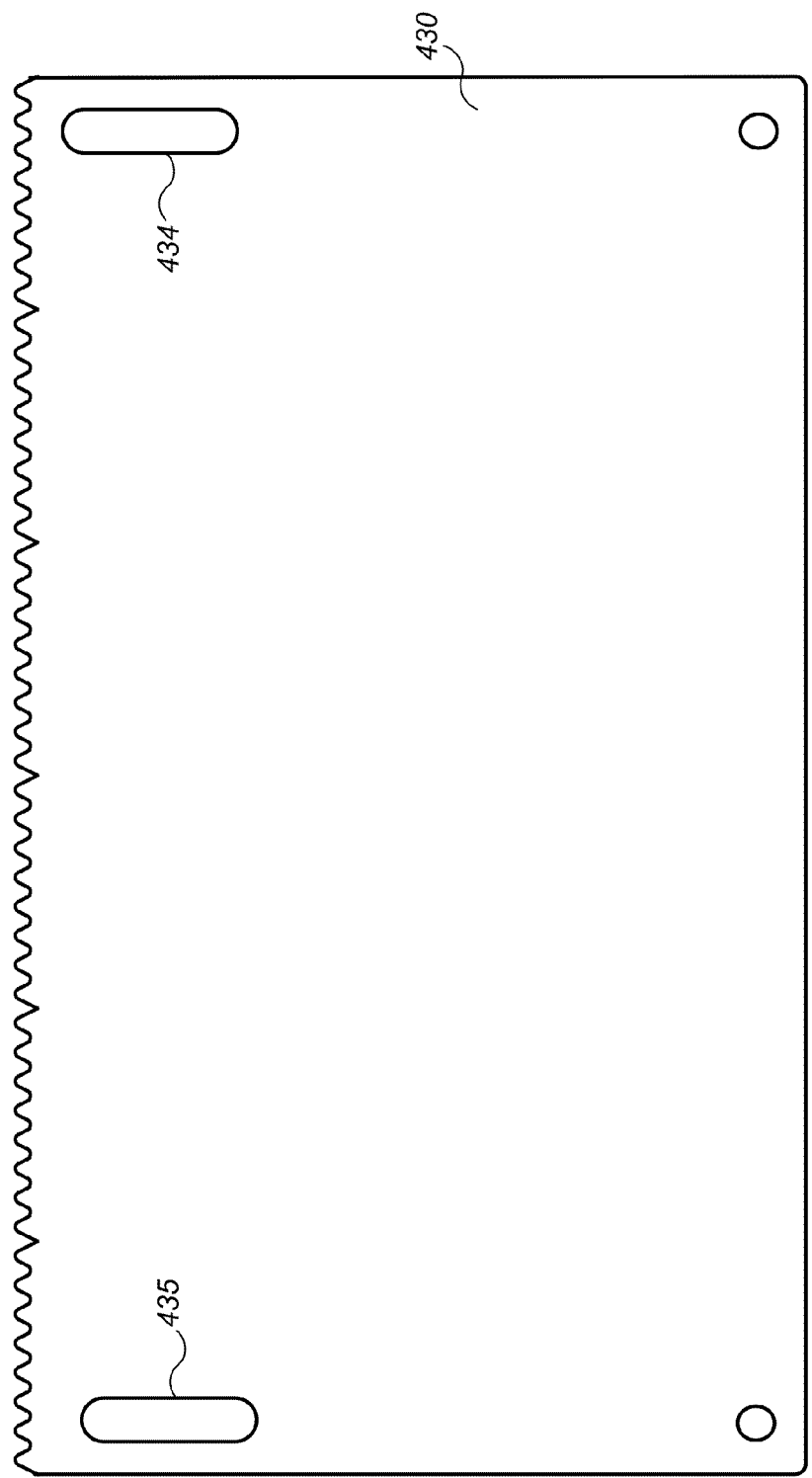

FIG. 4D illustrates a nit detection plate 430 according to a fourth example embodiment. The detection plate 430 includes cutouts 434 and 435. The cutouts 434 and 435 may be used in a manner similar to that described with reference to cutouts 414 and 415 of FIG. 4B. The cutouts 434 and 435 are, however, oriented in a manner substantially parallel to the hairs of the patient. The caregiver can place a clip through one or more of the cutouts 434 and 435 to attach the detection plate 430 to hairs of the patient. Again, by removably affixing the plate to the head/hair of the patient, the caregiver can advantageously perform some other function that requires the use of one or both of her hands.

Figure 4E:
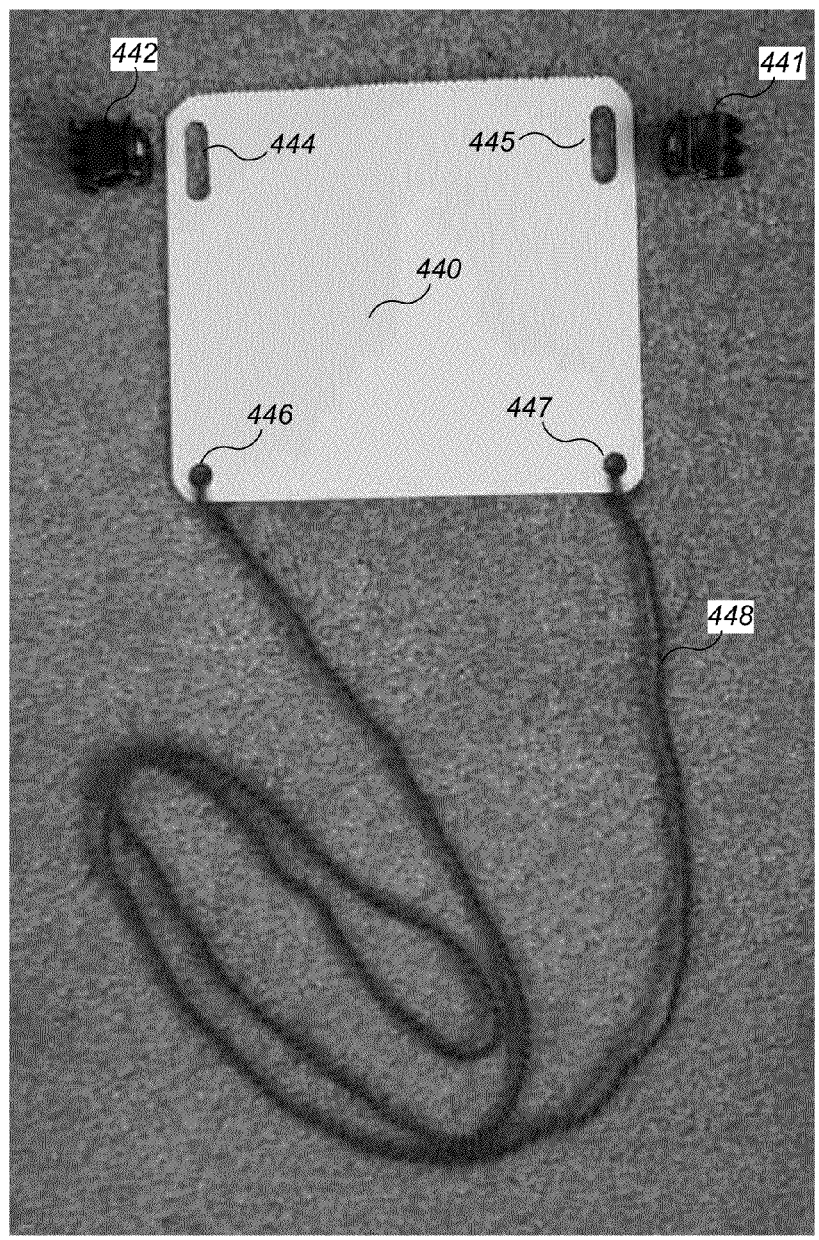
Figure 4F:
Figure 4G:

FIGS. 4E-4G illustrate a nit detection plate 440 according to a fifth example embodiment. As shown in FIG. 4E, the detection plate 440 includes cutouts 444 and 445 for attaching clips 441 and 442. The detection plate 440 further includes holes 446 and 447 for attaching a loop of string 448 or some other fastener. The clips 441 and 442 can be used as described above to fasten the detection plate 440 to the head or hair of the patient. In addition, the string 448 can be used as also described above to attach the plates 442 the body of the caregiver, such as by looping the string 448 over the head of the caregiver.

The example detection plate 440 is more than 5 inches (about 13 cm) measured along the side nearest cutout 444 and hole 446. By dimensioning the detection plate 440 thusly, it can be used to efficiently detect and remove nits that are located further away from the patient's scalp. Although nits are commonly found near the scalp (within 5 cm), and many treatments procedures focus on the near-scalp regions of the hair, nits are sometimes found further along the hair. As even a single nit can give rise to a new lice infestation, a relatively long (more than 10 cm, measured perpendicular to the serrated edge) detection plate can be considerably more effective at treating an existing infestation. Other dimensions may be employed. For example, some detection plates are at least 3 inches (about 8 cm) measured in each dimension of a substantially rectangular plate.

FIGS. 4F and 4G respectively illustrate substantially top and side views of the nit detection plate 440. In FIGS. 4F and 4G, the detection plate 440 is in place on, and affixed to, the head of a patient. The detection plate 440 is clipped to hairs of the head of the patient by way of clips 441 and 442. Note that in the configuration shown in FIGS. 4F and 4G, the caregiver can ungrasp the detection plate 440 in order to perform other functions such as removing a nit from one of the hairs of the patient. The detection plate 440, held in place by clips 441 and 442 will remain in place even as the caregiver uses both of her hands to remove a nit from one of the hairs of the patient, or performs some other function.

Various example embodiments have been shown and described above to better illustrate aspects of the nit detection plate. In other embodiments, a nit detection plate may include more or fewer features, be configured differently, be dimensioned differently, or be otherwise modified while still achieving the functions of a nit detection plate. For example, in one embodiment, a flexible arm may be included, the arm operable to hold a detection plate in position when not being held or grasped by the caregiver. The arm may be affixed to the caregiver, to the ground, to a table, or some other surface. In another embodiment, different types of clips or fasteners than those described above may be utilized.

As noted, one of the functions of the nit detection plate as to provide sufficient contrast to facilitate detection of nits. Typically the detection plate is made from a white or substantially white material. However other shades may also or instead be utilized, such as light gray or even pale colors (e.g., pale blue, pink, or green). The viewing qualities of the detection plate may be determined in various ways or terms, including whiteness (a measurement of light reflectance across all wavelengths of light comprising the visible spectrum), brightness (a measurement of light reflectance of a specific wavelength of blue light), and/or shade (a color measurement). In addition, the nit detection plate in some embodiments is made from a low gloss or matte material, such that the nit detection plate does not reflect an excessive amount of light or glare into the eyes of the caregiver, thereby reducing eye strain.

Furthermore, the nit detection plate in some embodiments is utilized with indirect rather than direct lighting. Indirect lighting may also reduce glare or other reflection from the nit detection plate to the eyes of the caregiver. In addition, experience has shown that nits may for some caregivers be easier to detect under indirect lighting conditions. In other embodiments, the nit detection plate may be made from a translucent material and include a backlight to facilitate the detection of nits.

In addition, although the terms "caregiver" and "patient" are used primarily herein, other terms may also or instead be substituted. For example, the term "patient" may include any person, animal, subject, or entity that is being treated according to the described techniques. Moreover, a "caregiver" need not be a medical professional (e.g., a doctor or a nurse), but includes any person administering treatment according to the described techniques. Furthermore, the terms "caregiver" and "patient" do not imply any particular relationship, such as a doctor-patient relationship, between the persons or entities administering and receiving treatment.

The described techniques may be applied in other contexts as well. For example, the described techniques may be used to detect and remove other types of biological material (e.g., burrs, seeds) from the hair of a person.

Figure 5A:
FIGS. 5A-5E illustrate an example nit removal process using a nit detection plate according to an example embodiment.

FIGS. 5A-5E illustrate an example nit removal process using a nit detection plate according to an example embodiment. In FIG. 5A, the hair of the patient 500 is prepared by using one or more clips 501 or other fasteners to lift, isolate, or locate patient hairs away from hairs 502 that are being examined for nits. In one embodiment, the hairs are first brushed/combed, and then parted into five or more sections. The sections may include the bangs, in front of the ears on the right side, in front of the ears on the left side, and two or more sections for the back of the head. The sections may be portioned so as to create a manageable section that is about 7-10 cm wide.

Figure 5B:

In FIG. 5B, a layer of hair 510 is isolated from other hairs of the patient by use of a comb handle 511 or other similar device. Once the caregiver isolates the layer of hair, the layer of hair 510 is grasped with the left hand 512 of the caregiver. The hair 510 will then be placed over a nit detection plate as described next. As discussed above, the layer of hair 510 is typically quite thin, such as about 2-5 mm in thickness, based at least in part on skill of the caretaker, qualities of the hair, lighting qualities, and/or the like.

Figure 5C:
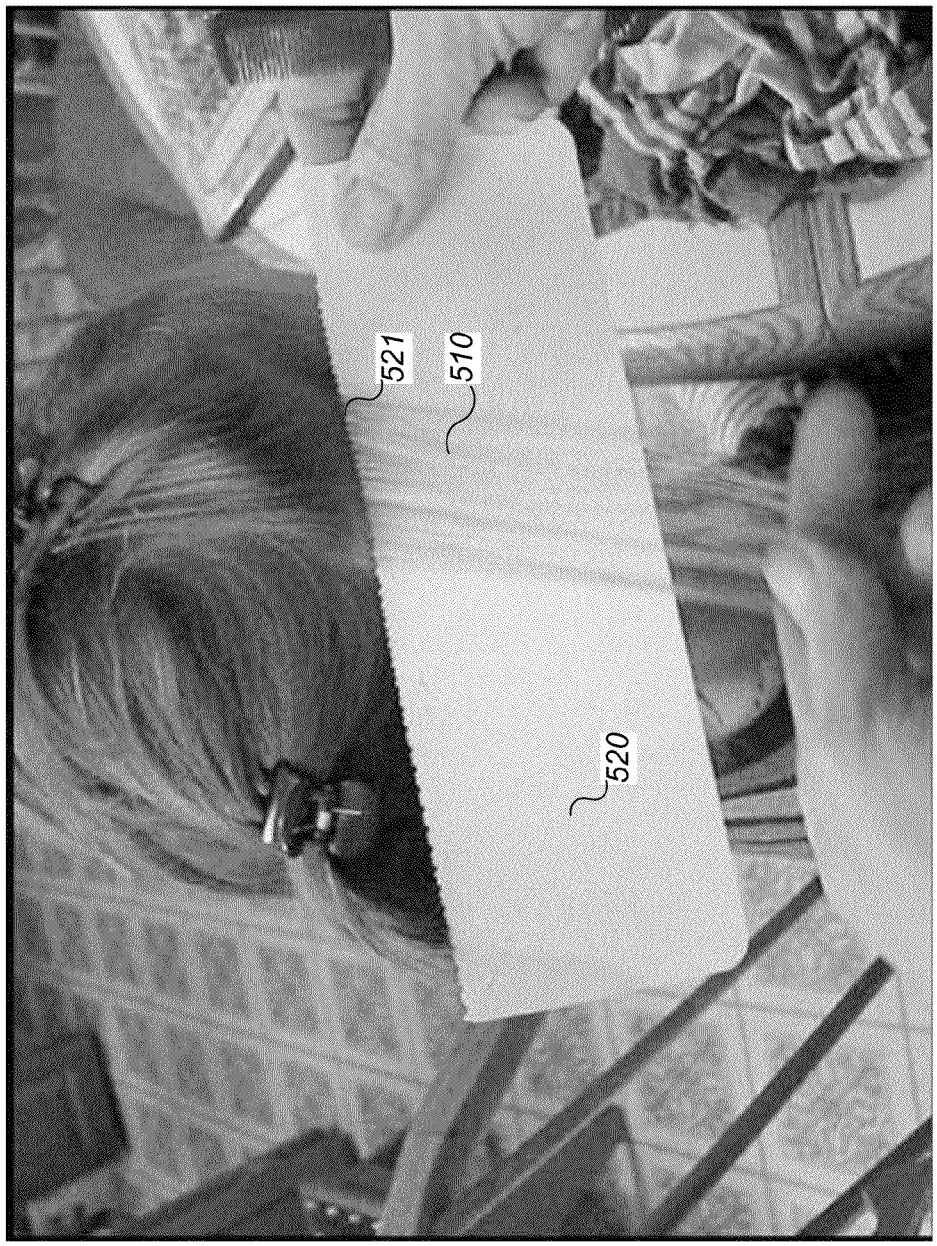

In FIG. 5C, the caregiver places a nit detection plate 520 under the layer of hair 510 isolated as described in FIG. 5B, above. Note how the hairs 510 are separated from one another by way of serrations 521 on the nit detection plate. At this point, the caregiver can manipulate the hairs 510 in various ways, such as by rolling the hairs 510 between her fingers or moving the hairs 510 from side to side. By manipulating the hairs 510 in this manner, nits that may be obscured by other hairs can be exposed to view.

In some embodiments, the caregiver employs a specific viewing or scanning technique to identify, detect, or locate nits. In particular, the caregiver does not continuously scan with her eyes in order to detect nits. Rather, the caregiver moves her eyes in discrete steps, pausing to focus on one region or area of the hairs 510 prior to moving her focus to another region. In at least some circumstances, this scanning technique results in improved detection of nits.

Figure 5D:

In FIG. 5D, the caregiver manipulates the nit detection plate 520 to further isolate hairs and to locate nits. In particular, the nit detection plate 520 may be moved from side to side (e.g., substantially back and forth along the long axis of plate 520), so as to spread out the hairs 510 and further expose nits to view. The nit detection plate 520 may also be reoriented with respect to the prevailing light source, so as to alter the lighting, contrast, and/or shading conditions. Furthermore, the nit detection plate 520 may be moved closer and/or further away from the caregiver (e.g., back and forth along the short axis of plate 520), so as to move the detection plate closer to the root of the hairs 510 or to move the nit detection plate 520 further down the length of the hairs 510.

Various other detection techniques are contemplated. In one embodiment, the hairs of a layer are held taught with one hand, while the caregiver "strums" the hairs with the thumb of the other hand, in order to separate the hairs and view them individually against the detection plate. In other embodiments, the caregiver holds the hairs of a layer up (towards the eyes of the caregiver), and views the hairs from their ends towards their roots, with the detection plate held downwards from the serrated edge placed near the roots of the hairs. This technique facilitates viewing the hairs against the detection plate from an additional angle. In further embodiments, the caregiver slowly releases hairs from the layer (e.g., from right to left), allowing them to drop onto the detection plate, while simultaneously viewing the dropping hairs for nits. In still other embodiments, the caregiver holds the detection plate along its non-serrated sides with both hands, keeping her thumbs on the top of the detection plate and the serrated edge against the scalp. The caregiver then users her thumbs to separate hairs from the top of the plate (nearest the roots to the bottom, continuing to view the hairs for nits as described above. In yet further embodiments, the caregiver rotates the detection plate against the scalp as needed to keep the serrated edge against the scalp. The caregiver moves detection plate slightly from side to side continuing to use the thumbs to separate and move the hairs. This serves to catch the hairs in the serrated edge of the detection plate and slightly rotates the hairs, thus revealing additional nits from yet more angles that may otherwise go unnoticed.

If a nit is detected at some point during the manipulations described with respect to FIGS. 5C and 5D, the nit can be removed. Various techniques for removal are contemplated. In one embodiment, the hair to which the nit is attached is cut from the head of the patient. In another embodiment, the nit is scraped from the hair to which it is attached, such as by pinching the nit/hair between a thumb and forefinger or similar sharp-edged device, and sliding the nit down and off the end of the hair.

As nits are detected and removed from the head of the patient they may be collected for accounting or recording purposes. In one embodiment, the caregiver places the nits, possibly with hairs still attached, into a white or substantially white container that provides high contrast for viewing. By placing the nits in a high contrast container, they can be easily counted at the end of a treatment cycle or phase. By counting the nits collected during a treatment cycle, the caregiver can determine whether progress is being made against an infestation by comparing the number of nits collected during a current treatment cycle against one or more previous treatment cycles. If the number of nits collected over time is decreasing, then the caregiver has obtained evidence that the infestation is subsiding and/or that the caregiver is effectively detecting and removing nits and killing nymphs and adult laying lice. In addition, when the number of nits reaches zero or some other very low number (e.g., one, two, five), the caregiver has obtained evidence that the infestation is at or near its end, because it is highly unlikely that a new generation of lice will be born and further inhabit and infest the hair the patient, provided the described nit detection plate is being used.

Figure 5E:

In FIG. 5E, the caregiver takes the layer of hair 510 that was examined as described above and groups it with the hairs previously isolated as described with respect to FIG. 5A. For example, the caregiver can add the layer of hair 510 to the hairs previously isolated by way of clip 501. Then, the caregiver can continue the cycle of detection and removal by isolating a new layer of hair as in FIG. 5B, and examining the new layer of hair as described with respect to FIGS. 5C and 5D. The caregiver typically continues this procedure until all or substantially all of the hairs of the patient have been examined for nits, including small hairs along the neckline and by the ears, eyebrows, and eyelashes.

FIG. 6 illustrates a lice infestation treatment process according to an example embodiment. The illustrated process is typically performed by a caregiver over the course of several weeks. In FIG. 6, time is depicted via timeline 610. Although in some cases particular operations are described as being performed over a specific number of days or on a specific day, in other embodiments the operations may be performed over a shorter or longer period of time, or on different days. By way of overview, the process includes five overlapping phases or operations, including cleaning of the patient's residence, treating hair for live lice, collecting and recording dead lice, detecting and removing nits, and confirming the presence/absence of nits.

The process begins at block 600, where four parallel operations are initiated, as described with respect to blocks 601, 602, 603, and 604. At block 601, the caregiver treats the patient's residence. Treating the patient's residence typically includes one or more of: washing clothing, towels, and linens in hot water (e.g., over 130 degrees F.); storing clothing, towels, linen, pillows, soft toys, and the like in sealed plastic garbage bags for a week or more; vacuuming furniture, carpets, rugs, soft toys, and the like; cleaning (e.g., wiping and/or vacuuming) the inside of a vehicle; and the like.

At block 602, the caregiver treats the patient's hair for live lice. Treating the hair for live lice is in this example performed on days 1, 2, and 3. The hair is treated on multiple successive days in order to increase the chances of killing all live lice, including those that may have survived a previous treatment and/or those that may have arrived after the previous treatment. In one embodiment, treating the hair for live lice includes suffocating the lice by coating the hair in some type of oil (e.g., olive oil, vegetable oil, shortening) for an extended period of time (e.g., overnight). For example, the hair may be soaked in olive oil overnight or for at least eight hours, by applying oil throughout the hair, and then placing a shower cap or other covering over the patient's oil-soaked head. In other embodiments, commercially prepared toxic or non-toxic treatment products may be employed to kill live lice.

At block 603, the caregiver collects and records dead lice. Collection and recording of lice is performed on each day after the hair is treated for live lice as described with respect to block 602. For example, where the hair is treated for live lice by soaking in oil overnight, block 603 is performed on days 2, 3, and 4. In one embodiment, the substance (e.g., oil, poison) used to kill the live lice in block 602 is removed from the patient's hair along with any lice killed by the substance. The dead lice are then counted and recorded. For example, after soaking the patient's hair with olive oil, the patient's hair may be washed using dishwashing soap, shampoo, or some other substance operable to remove the olive oil. In one embodiment, a non-toxic dishwashing soap, such as Dishmate™ dish soap is utilized for this purpose. After soap is applied to and massaged into the patient's hairs, the hairs are rinsed into a vessel that is at least closed to outflow of liquid (e.g., a sink, a bathtub). In addition, it may be advantageous to first massage handfuls of soap directly into oiled, but non-wetted, hair and to bring the soap to lather prior to rinsing and washing the hair with water. Such an approach may more effectively break down the oil in the patient's hair, yielding non-oily hair that can be more efficiently processed using the nit detection and removal techniques described herein. Once the hairs are thoroughly rinsed into the vessel, a device that includes a trap, net, mesh, screen, or filter may be employed to collect or catch dead lice before they are washed out of the vessel as liquid is released therefrom. In some embodiments, a defoamer (e.g., containing a surfactant) may be used to dissolve or break down soap bubbles which may hide or otherwise obscure view of dead lice. The dead lice are collected and counted so that a total of lice killed on each treatment day may be recorded. Dead lice found on the inside of a shower cap or other head covering used during lice suffocation are also counted and recorded. Once the hair is washed and free of oily residue, it is thoroughly dried. In some embodiments, the patient's hair may be combed with a fine-toothed comb, such as before the hair is washed to remove additional nits, prior to using the nit detection plate describe herein.

At block 604 the caregiver detects and removes nits. While blocks 602 and 603 serve to eradicate live lice, block 604 serves to eradicate the next generation of lice by searching for and destroying nits. Nit detection and removal is performed by a method such as that illustrated and described with respect to FIGS. 5A-5E, above, and the flow diagram of FIG. 7, below. Nit detection and removal is performed on each day after the hair is treated for live lice (block 602) and dead lice are collected and recorded (block 603). In addition, nit detection and removal is performed one or more days after the completion of blocks 601 and 602. Thus, in this example, nit detection and removal is performed on days 2-4 after blocks 602 and 603, and on days 5 and 6 without performance of blocks 602 or 603 on those days. In addition, as discussed next, nit detection is performed a number of times after the termination of block 604, in order to determine whether the treatment has been successful, and to restart treatment if not.

By the fifth day, the caregiver will typically no longer be detecting any nits (and/or lice) in the patient's hair. Starting on the fifth day in this example, the process enters a confirmation phase, during which the patient's hair is checked for nits or lice one or more times to determine whether the treatment has been successful. Checking for nits and/or lice may also be performed using the detection plate, as described herein. In this example, at blocks 605-609, the caregiver checks the patient's hair for nits and/or lice on days 5, 6, 10, 14, and 18, respectively. If, on any of these days, the caregiver confirms the presence of nits or lice, the process returns to block 600 to begin the treatment anew. If, on day 18, it is determined that there are no nits or lice in the patient's hair, the process ends as a successful treatment.

The process of FIG. 6 is advantageously adapted to disrupt the louse reproductive lifecycle. In particular, nit detection and removal (block 604) is performed over multiple successive days after an initial phase of treatment for live lice (blocks 602 and 603). By detecting and removing nits over multiple successive days, the chances of eliminating all potentially viable nits, which would otherwise result in a new generation of lice, are greatly improved. In addition, as it can take up to 14 days for a nit to hatch into a nymph louse, the process checks for nits or lice (e.g., blocks 607-609) up to or even over 14 days after the initial phase of lice treatment is completed.

The process of FIG. 6 includes operations that are performed in a specific order, for specific durations, and at specific times. The operations and their timing may be varied in other embodiments. For example, in other embodiments, the lice infestation treatment process may include a greater or lesser number of confirmation operations (e.g., blocks 605-609) and these operations may be performed on different days than shown in FIG. 6. Also, blocks 601-604 may be performed over a longer or shorter time period. For example, nit detection and removal may be performed over days 2-5, days 2-8, or the like.

Figure 7:
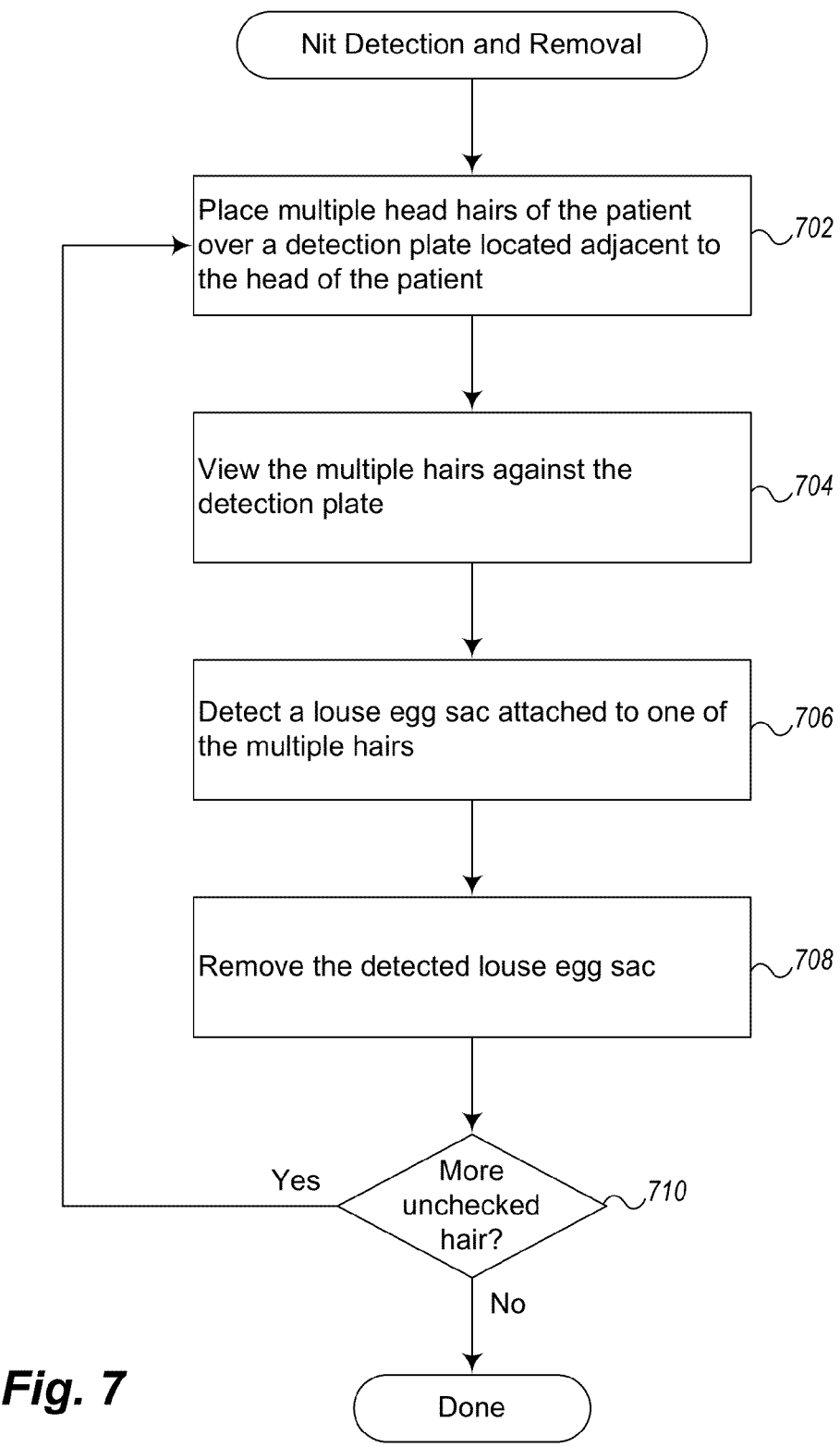
FIG. 7 is an example flow diagram of a nit removal process performed according to an example embodiment.

FIG. 7 is an example flow diagram of a nit detection and removal process performed according to an example embodiment. The illustrated process may be performed by a caregiver, such as within the context (e.g., block 604) of the process for treating a lice infestation described with respect to FIG. 6, above.

The process begins at block 702, where a caregiver places multiple head hairs of the patient over a detection plate located adjacent to the head of the patient. Placing multiple head hairs over the detection plate may include placing a thin layer of hair over the detection plate. The thickness of the layer may be selected by the caregiver based on various factors, including lighting conditions, characteristics of the hair (e.g., oil content, color), the caregiver's skill level, and the like.

At block 704, the caregiver views the multiple hairs against the detection plate. The multiple hairs are thus positioned between the caregiver's eyes and the detection plate, so that the detection plate forms a background for viewing the hairs. In one embodiment, viewing the multiple hairs may include a discrete scanning technique in which a first region of the detection plate is viewed for a time period (e.g., 3 seconds 5 seconds 10 seconds) prior to shifting the caregiver's view and focusing on a second region of the detection plate. The caregiver's eyes thus move in discrete, rather than continuous motion while scanning the hair for nits.

At block 706, the caregiver detects a louse egg sac that is attached to one of the multiple hairs. At block 708, the caregiver removes the detected louse egg sac. Egg sacs may be removed in various ways. In one embodiment, removing an egg sac may include cutting the hair to which egg sac is attached from the head of the patient. In another embodiment, the egg sac may be scraped off its associated hair by way of pinched fingernails or other sharp edged device.

At block 710, the caregiver determines whether there is more unchecked hair, and if so, continues checking for and removing nits at block 702. Otherwise, the caregiver has checked all or substantially all of the hairs of the patient, and the process ends.

Other steps may be performed in addition to, or instead of, the operations described above. In one embodiment, nits that are removed from the patient's hair are collected and counted. The nits may be collected in a bright or high contrast container such as an empty white yogurt container. By collecting and counting the nits removed by way of the illustrated process, the caregiver can determine from day-to-day whether treatment has been or is likely to be effective. For example, if the caregiver notices a sharp increase in the number of nits removed, the caregiver may suspect a re-infestation of live lice.

In addition, the process may be modified to function as a nit detection process, such as may be performed at blocks 604-606 of FIG. 6. In particular, the process can function as a nit detection process by using the described detection techniques, but terminating the loop of steps 702-710 as soon as one or more nits have been detected, without necessarily removing the detected nits (block 708).

In some embodiments, a lice infestation treatment kit is provided. The treatment kit may include one or more of the following items: a nit detection plate; attachment mechanisms (e.g., clips, strings, bands, stands) for attaching the detection plate to the patient and/or the caregiver; one or more combs; instructions detailing at least some of the above-described techniques; a calendar that provides day-to-day instructions and/or locations for recording the numbers of lice or nits collected on each day; a substantially white container for collecting lice and/or nits; and the like.

In some embodiments, a network-accessible service is provided to support or facilitate treatment of head lice. The service may include or provide additional instructions; an online forum (e.g., a chatroom, Web forum) where caregivers can share experiences and/or trade advice; a store front where customers can purchase treatment kits, detection plates, or other devices for treating lice infestations; or the like. In some embodiments, a uniform resource locator ("URL") or similar identifier may be provided along with a treatment kit to direct customers or caregivers to the service. The service may be implemented as a Web site hosted by one or more servers executing on a computing system. The service may be accessible via a Web browser or other application (e.g., a mobile application) executing on a client computing device (e.g., a home computer, a smart phone, a laptop).

All of the above U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/505,359, entitled "TREATMENT OF HEAD LICE INFESTATIONS," filed Jul. 7, 2011, is incorporated herein by reference, in its entirety.

From the foregoing it will be appreciated that, although specific embodiments have been described herein for purposes of illustration, various modifications may be made without deviating from the spirit and scope of this disclosure. For example, the methods, techniques, and apparatus for lice infestation treatment are applicable in other contexts. For example, even though the techniques have been primarily described with respect to head lice, at least some of them may be employed to treat pubic lice. Also, the techniques may be employed with animals other than humans, such as chimpanzees or dogs.

The invention claimed is:

1. A method for treating a head lice infestation in a person, the method comprising:
    placing multiple head hairs of the person in front of a detection plate located adjacent to the head of the patient, the detection plate providing a contrasting background against which irregularities of a hair are more apparent to a viewer than without the detection plate;
    viewing the multiple hairs against the detection plate;
    detecting a louse egg sac attached to one of the multiple hairs; and
    removing the louse egg sac,
    wherein placing the multiple hairs of the person includes positioning the multiple hairs between eyes of a viewer and the detection plate, such that the detection plate provides a background against which the viewer can examine the multiple hairs for the presence of lice eggs.

2. The method of claim 1, the detection plate including:
    a serrated edge configured to separate hairs of the person.

3. The method of claim 2 wherein serrations of the serrated edge are no more than 2mm in height and separation.

4. The method of claim 2 wherein serrations of the serrated edge are between 1and 3mm in separation.

5. The method of claim 1, the detection plate further comprising:
    one or more fasteners operable to removably affix the detection plate to hair of the person, such that a person using the detection plate can release the detection plate while removing a louse egg sac from the hair of the person.

6. The method of claim 1 wherein the detection plate is substantially white in color.

7. The method of claim 1 wherein the detection plate is substantially rectangular in shape and is at least 8 cm in width and in length.

8. The method of claim 1 wherein the detection plate has a matte surface.

9. The method of claim 1 wherein placing the multiple hairs of the person in front of the detection plate includes placing a layer of hairs, the layer being no more than 3mm in thickness.

10. The method of claim 1, further comprising:
    manipulating the multiple hairs during the viewing of the multiple hairs, the manipulating including at least one of rolling, shifting, and/or sliding the hairs over the detection plate.

11. The method of claim 1 wherein viewing the multiple hairs includes scanning regions of the detection plate in discrete steps and not in a continuous motion.

12. The method of claim 1 wherein removing the louse egg sac includes cutting the one hair off of the head of the person.

13. The method of claim 1, further comprising:
    removing hairs from the person, the removed hairs attached to lice egg sacs;
    collecting the removed hairs in a substantially white container;
    determining a number of lice eggs removed by counting the removed hairs and/or attached lice egg sacs; and
    recording the determined number of lice eggs.

14. The method of claim 1, further comprising:
    performing the method over substantially all of the hairs of the person.

15. The method of claim 1, further comprising:
    treating the hair for live lice on one or more days; and
    performing the method on multiple days over a period of time that is at least one week in length.

16. The method of claim 15, further comprising:
    after the performing the method on multiple times over the period of time, examining hairs of the person using the detection plate to determine whether or not lice or lice eggs are present.

17. The method of claim 16, further comprising:
    if it is determined that no lice or lice eggs are present, determining that the lice infestation has been successfully treated.

18. The method of claim 16, further comprising:
    if it is determined that lice or lice eggs are present, re-treating the hair for live lice on one or more days.

19. The method of claim 16 wherein the detection plate includes a serrated edge, and further comprising:
    placing the serrated edge of the detection plate against the head of the person and adjacent to roots of the multiple hairs; and
    fastening the detection plate to hairs of the person.

* * * * *